United States Patent [19]
Wang et al.

[11] Patent Number: 6,001,312
[45] Date of Patent: Dec. 14, 1999

[54] REACTOR FOR MAKING UNIFORM CAPSULES

[76] Inventors: Taylor G. Wang, 4999 Tyne Ridge Ct., Nashville, Tenn. 37220; Amrutur V. Anikumar, 6925 Harpeth Glen Trace, Nashville, Tenn. 37221; Igor Lacik, Bystricka 34, 90201 Pezinok, Slovakia

[21] Appl. No.: 08/843,516

[22] Filed: Apr. 16, 1997

Related U.S. Application Data

[60] Provisional application No. 60/015,593, Apr. 17, 1996, provisional application No. 60/015,791, Apr. 17, 1996, and provisional application No. 60/015,795, Apr. 17, 1996.

[51] Int. Cl.$^6$ ..................................................... B01J 13/02
[52] U.S. Cl. .......................... 422/131; 526/918; 264/4.33; 264/4.7; 427/213.34
[58] Field of Search ............................ 422/131; 526/918; 264/4.7, 4.3, 4.33; 427/213.34

[56] References Cited

U.S. PATENT DOCUMENTS 4,454,083  6/1984  Brown et al. .................. 427/213.34 X
5,720,923  2/1998  Haff et al. ............................... 422/68.1

*Primary Examiner*—Elizabeth McKane
*Attorney, Agent, or Firm*—Benjamin Aaron Adler

[57]  ABSTRACT

The present invention provides a novel reactor for making capsules with uniform membrane. The reactor includes a source for providing a continuous flow of a first liquid through the reactor; a source for delivering a steady stream of drops of a second liquid to the entrance of the reactor; a main tube portion having at least one loop, and an exit opening, where the exit opening is at a height substantially equal to the entrance. In addition, a method for using the novel reactor is provided. This method involves providing a continuous stream of a first liquid; introducing uniformly-sized drops of the second liquid into the stream of the first liquid; allowing the drops to react in the stream for a pre-determined period of time; and collecting the capsules.

4 Claims, 12 Drawing Sheets

REACTOR FOR MAKING UNIFORM CAPSULES

CROSS-REFERENCE TO RELATED APPLICATIONS

This application is a continuation of U.S. provisional patent application 60/015,593, filed Apr. 17, 1996, U.S. provisional patent application 60/015,791, filed Apr. 17, 1996, and U.S. provisional patent application 60/015,795, filed Apr. 17, 1996.

FEDERAL FUNDING LEGEND

This invention was produced in part using funds from the Federal government under grant no. NIH DK20593 and under JPL (Jet Propulsion Labratory) subcontract No. 958972 under NASA contract NAS7-918. Accordingly, the Federal government has certain rights in this invention.

BACKGROUND OF THE INVENTION

1. Field of the Invention

The present invention relates generally to the field of biomedical engineering. More specifically, the present invention relates to a novel reactor for making uniform capsules.

2. Description of the Related Art

Capsules, with semipermeable polymer membranes as their walls, have been employed as the media for a variety of medical applications, such as controlled release of medicines and immunoisolation of hormone-producing cells, such as pancreatic islets, etc. Polymer membrane design and the selection of the capsule inner liquid is being researched continuously.

The methodology of conventional capsule production involves the interaction of two reacting (oppositely charged) polymers, a drop of one in a bath of the other, leading to polyelectrolyte complex (membrane) formation. The reaction is turned off by quenching the capsule in a buffer after the appropriate reaction time (once an appropriate thickness of membrane has formed). The concentrations of the polymers influence the membrane qualities and permeability. The strength of the capsule and its immunoisolation efficiency is a function of its thickness, which depends on reaction time. Physically, the membrane functions as a flow regulator or molecular sieve, allowing passage of some molecules or retention of others, based on the size of the molecule.

An example of this methodology is as follows: assume that anion drops react with a cation bath to form capsules. If desired, the anion drops carry the encapsulant. A steady stream of anion drops can be produced by a variety of techniques. When anion viscosities are low (<50 cS), capillary wave excitation on the anion jet and subsequent development of instability of the jet leads to precisely partitioned anion drops. However, when anion viscosities are higher, and especially while dealing with polymers, the more flexible route to drop production is through air stripping (see FIG. 1), wherein uniformly-sized drops are produced. In air stripping, individual drops are sheared off the nozzle by the air stream, and in principle, there is no restriction imposed on the rate of pumping of the anion (no need to pump a jet) and a rate of anion delivery can b e selected to suit the encapsulation needs. The only draw back to air stripping is that the drop pointing accuracy is not perfect and, depending on the anion viscosity, the trajectories of the stripped drops encompass a small cone angle.

One current goal is to make uniform capsules from anion drops of uniform size, produced at a controlled rate. A conventional approach is to collect the anion drops in a bath of cation in a beaker. The problem with this approach is that when reaction rates are fast, such that the times for collection and reaction are very comparable, then the resulting capsules have varying wall thicknesses. For example, if the batch collection time is 30 seconds and the selected reaction time is 30 seconds, then the first capsule would have reacted for 60 seconds, whereas the last capsule would have reacted for only 30 seconds. Furthermore, since the cation in the beaker is continuously depleted by the reacting anion drops, the concentration of the cation is different between the first capsule and the last. This leads to heterogeneity in wall thickness, and membrane properties, between capsules (FIG. 2). Therefore, to minimize variability, one would have to keep the collection time much smaller than the reaction time. This can be problematic, if a large volume production is desired, whether in a laboratory or industrial setting. Another way to minimize variability is to slow down the anion-cation reaction rates, by diluting the concentrations of either, or both, or by other chemical means. Dilution, however, is not always possible without losing desired properties of the polymers. Also, with the conventional approach, when there is a substantial density mismatch between the anion drop and the cation solution, the capsule walls do not form uniformly around the drop. This is because during processing, the capsules will either settle at the bottom of the beaker or collect at the top interface. Stirring does not always solve this problem.

The goal for capsule production is now well defined; viz., to design an apparatus that can continuously generate capsules at a high rate, with precise control of reaction time, and with uniform exposure of the developing capsule to the cation. Clearly, it is preferable that such an apparatus would require very little attention during operation. Additionally, the economy of cation usage merits consideration, for the cation can be expensive and neutralizing large volumes of cation with buffer to stop the reaction is very cumbersome.

The prior art is deficient in the lack of an effective capsule producing apparatus that continuously can generate uniform capsules at a high rate of production with very little monitoring. The present invention fulfills this longstanding need and desire in the art.

SUMMARY OF THE INVENTION

A novel chemical reactor has been designed and developed to make uniform capsules continuously at a high rate of production. Using the reactor of the present invention, one can precisely control the reaction time between reacting liquids (anion drops and a cation bath, or vice versa), thereby leading to uniform-sized capsules, with walls of each capsule having identical thickness and qualities. In addition, the mild tumbling of the capsule during transit through the reactor ensures that the thickness of the wall of each individual capsule is uniform all around.

In one aspect of the present invention, there is provided a reactor for making capsules, comprising: means for providing a continuous flow of a first liquid through said reactor; means for delivering a steady stream of drops of a second liquid to an entrance opening of said reactor; a main tube portion, where the tube portion has at least one loop and at least two openings, where one of the openings is at a first end of the tube and is the entrance opening, and where the other opening is at the second end of the tube and is an exit, and where the exit is at a height substantially equal to the entrance; and a collector at said exit opening. In a preferred embodiment, the entrance opening has a funnel shape. In yet another embodiment of the present invention, the exit is connected to a second tube portion with at least one, and perhaps several loops, where the second tube portion has at least three openings, a first opening for collection of said capsules, a second opening for introducing buffer into said second tube portion so as to create a buffer stream, and a third opening for rendering said capsules treated in said buffer stream in said second tube portion.

In another aspect of the present invention, there is provided a method of making capsules, comprising: providing a continuous stream of a first liquid; introducing uniformly-sized drops of a second liquid into said continuous stream of the first liquid; allowing the uniformly-sized drops to react in the continuous stream for an appropriate period of time to form capsules; and collecting the formed capsules. In certain instances, it may be advantageous to subsequently quench the capsules in buffer, or soak them in a leeching agent. In a preferred embodiment, the stream of the first liquid is delivered by using compressed air, and the drops of the second liquid are produced by air stripping.

In the method of the present invention, a cation/anion system may be used. If so, preferred embodiments are thus: if the first liquid is a cation, the second liquid is an anion; and when the first liquid is an anion, the second liquid is a cation. In addition, it is preferred that the densities of the first liquid and second liquids be similar.

In a preferred embodiment of the method of the present invention, the convective velocity ($U_C$) of the capsule is greater than the sedimentation velocity ($U_S$) of the capsules. In a more preferred embodiment, the radial component of the sedimentation velocity is such that the radial traverse is less than the inner diameter of the tube bore, during the transit of the capsule through half of the loop.

In the present method, it is preferred the convective velocity ($U_C$) and sedimentation velocity ($U_S$) be related such that $U_C > K D/d U_S$; wherein D equals a diameter of said loop, d equals a bore diameter of said tube, and K is a constant.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention can be understood in detail, more particular descriptions of the invention may be had by reference to certain embodiments which are illustrated in the appended drawings. These drawings form a part of the specification. It is to b e noted, however, that the appended drawings illustrate preferred embodiments of the invention and therefore are not to be considered limiting in their scope.

DETAILED DESCRIPTION OF THE INVENTION

In the description of the present invention, the following abbreviations may be used: SA=sodium alginate; CS, cellulose sulfate; PMCG, poly(methylene-co-guanidine); PBS, phosphate-buffered saline; $CaCl_2$, calcium chloride; NaCl, sodium chloride.

As used herein, the term "flux" refers to the flow rate in the reactor, typically expressed in cc/min.

As used herein, the term "hydrostatic head" refers to the constant difference in fluid levels between the entry and exit of the reactor, that corresponds to a hydrostatic pressure difference pgη, representing the pressure loss through the reactor.

As used herein the term "trajectory" refers to the path followed by a capsule.

As used herein, the term "critical volume flux" refers to the lowest cation flow rate at which capsules barely make it through a reactor without stalling.

As used herein, the term "capsule stall" refers to gravitational settling of capsules on the reactor inner walls, due to insufficient volume flux to convect them in the reactor.

As used herein, the term "consumption pattern" refers to the rate of usage/consumption of cation in a particular run of the experiment.

As used herein, the term "laminar flow" refers to smooth, steady, quiescent flow inside the reactor tube as opposed to fluctuating and agitated turbulent flow.

As used herein the term "Hagen Poiseuille flow" refers to fully-developed laminar flow in tubes, with the flow profile being a parboloid, falling to zero at the walls and reaching maximum at the central axis.

The present invention is directed to a novel capsule reactor that effectively can meet most process demands and deliver uniform capsules continuously at a high rate of production. The operating characteristics of the apparatus and the fundamental fluid dynamic principles guiding the operation are described. The starting point for the design is based on the very basic principle that a liquid, in a container opened to the same ambient pressure at more than one point, seeks an identical level at each opening.

Thus, the present invention is directed to a reactor for preparing capsules of uniform size and wall thickness, and a method of preparing same.

The following examples are given for the purpose of illustrating various embodiments of the invention and are not meant to limit the present invention in any fashion.

EXAMPLE 1
Reactor Design And Operation

Figure 1:
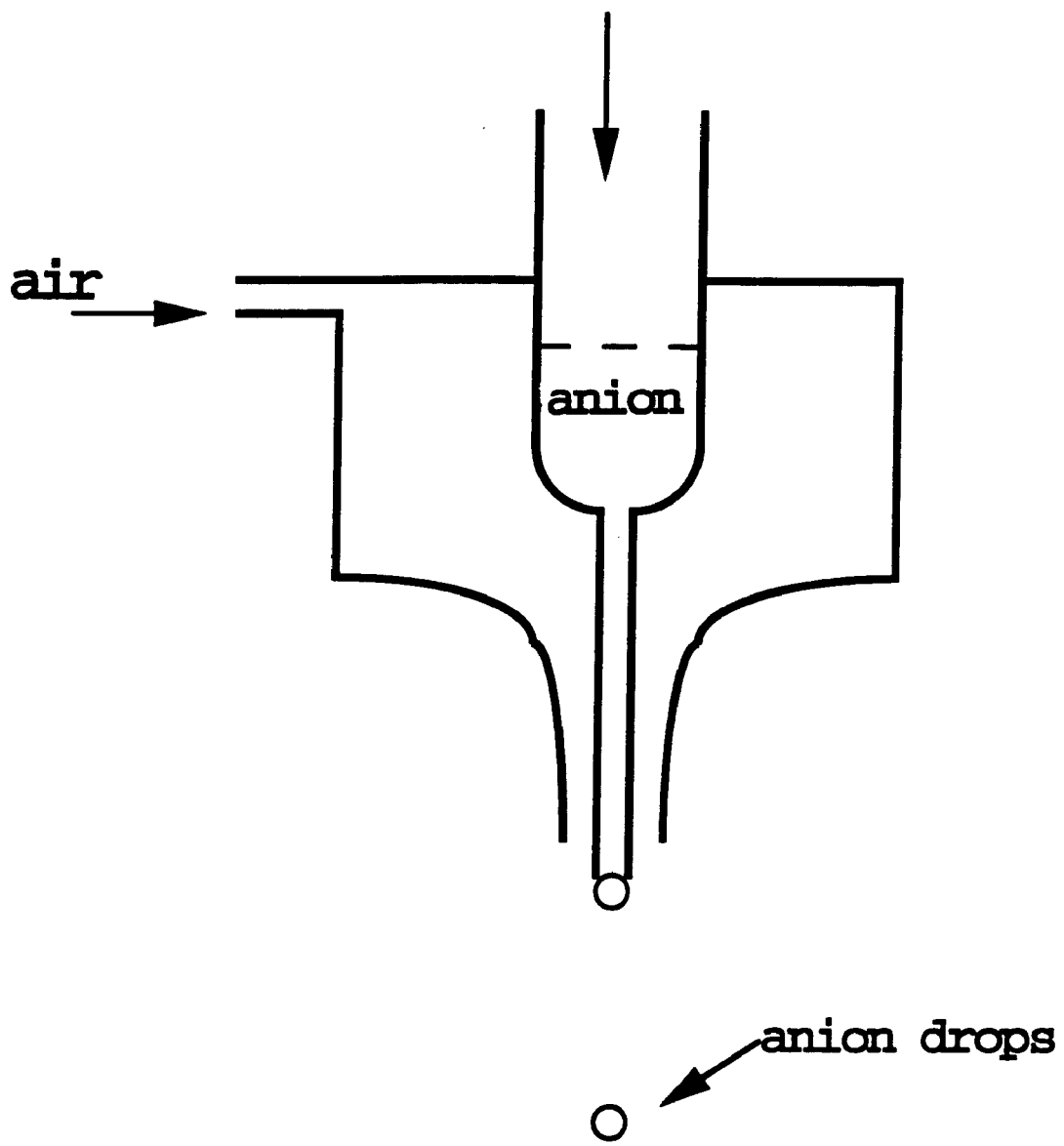
FIG. 1 shows an air stripper used for generating uniform anion drops.
Figure 2:
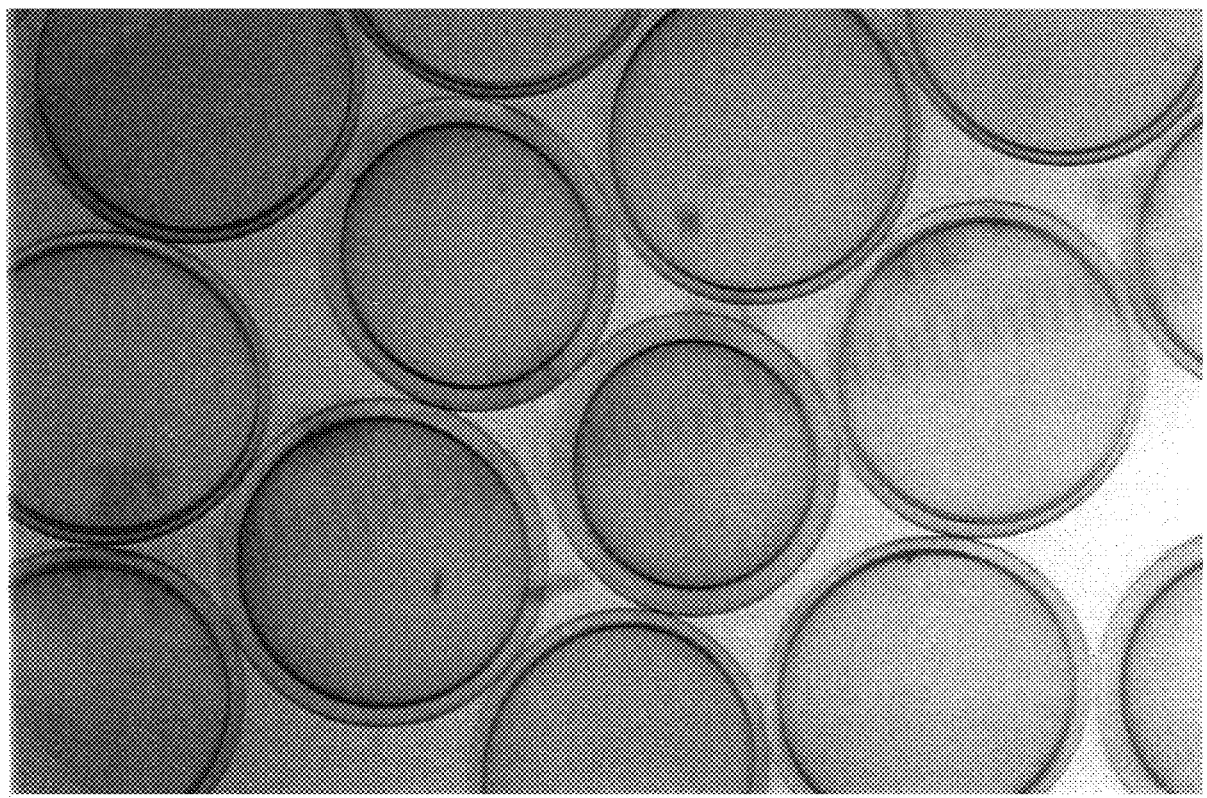
FIG. 2 shows the heterogeneous capsules (varying wall thicknesses) produced in conventional beaker collection and reaction. In this instance, collection time was 30 seconds and reaction time was 30 seconds.
Figure 3A:
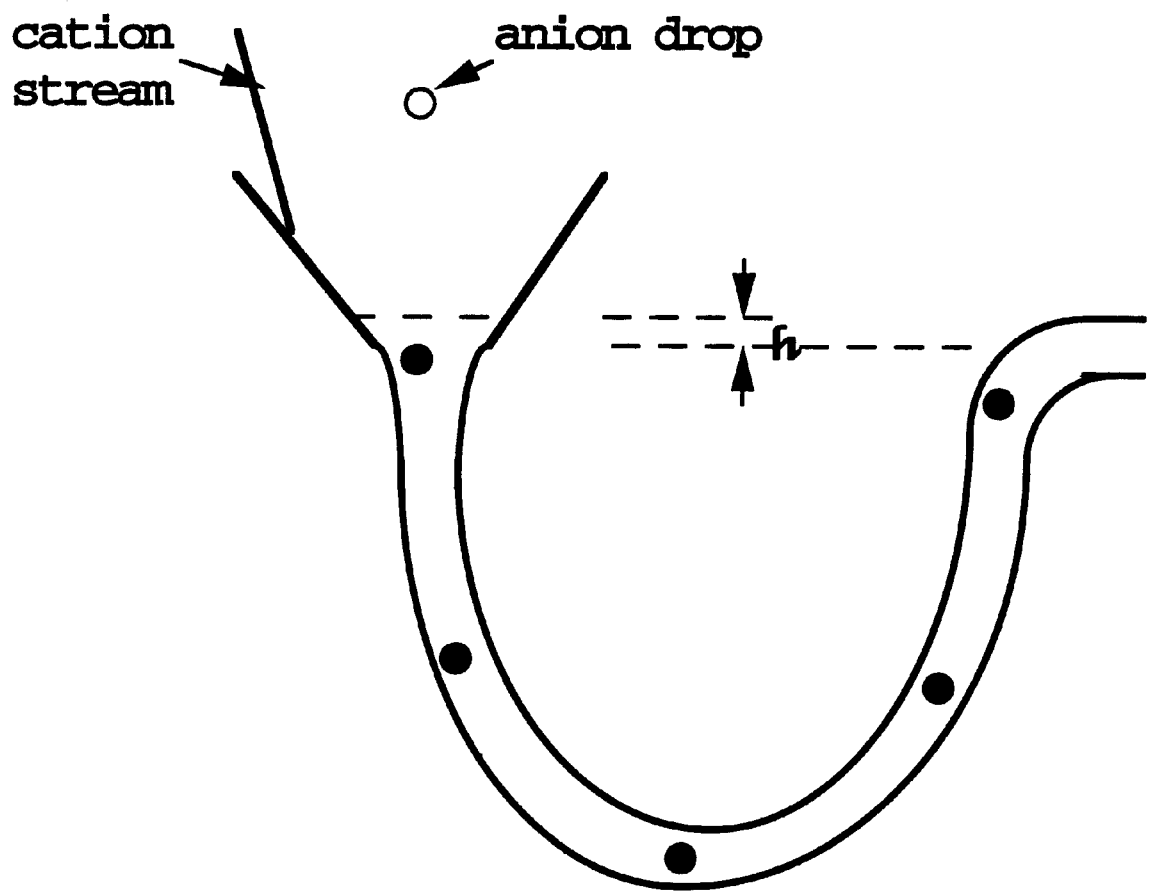
FIGS. 3a and b show the schematic of (a) a single-loop capsule reactor, and (b) the complete experimental layout for generating uniform capsules, with a multi-loop reactor.

FIG. 3A shows a schematic of the novel capsule reactor, with a single loop. Generally, the greater the reaction time required, the greater the number of loops in the reactor. A single loop reactor is described to facilitate understanding of the basic operating principles of the reactor.

The principle is based on the following: if the loop was filled with cation liquid with no air bubbles in the loop, the level of the cation in the funnel would remain at the level of the exit opening because both the opening of the funnel and the exit opening are subject to the same atmospheric pressure. If the exit were lower, the level of cation liquid in the funnel section would also be lower. If a steady stream of cation liquid (preferably as a thin, quiescent sheet along the funnel walls) is introduced into the funnel, after a short period of time for transient adjustment of the level of the liquid in the funnel, the liquid flows out of the exit at the same rate. The level of the cation in the funnel is now a little higher than earlier, by a height $\eta$ (hydrostatic pressure $\rho g \eta$), to compensate for the pressure loss due to the flow of the liquid through the tube. If the cation flux is higher, then the hydrostatic head $\eta$ is higher. The pressure loss through the loop also depends on the diameter of the tube bore and the number of loops. If the bore is smaller, or the number of loops higher, then the pressure loss is higher and so would be the hydrostatic head. Depending on the operating conditions and requirements, this flow device is self adjusting.

The procedure for generating uniform capsules in such a self-adjusting flow device occurs as in the following scenario: A steady stream of anion liquid drops into a funnel. The funnel is needed because the drops stripped by air do not take precisely the same trajectory. The trajectories of the drops after air stripping are actually similar in formation to a small cone angle. After being dropped into the funnel, the anion drops are drawn into the cation stream, ride through the tube, react along the way and exit at the other end (see FIG. 3B). Following exit, the reaction is quenched by a buffer medium, either in a bath as pictured or in an additional looped-stream. Along the transport of the anion drop through the reactor, transformation occurs in which a drop is transformed into a capsule of precise wall thickness and properties. The forming capsules tumble mildly in the flow, which results in uniform, circumferential exposure to the cation flow, generating a uniformly thick wall.

As long as the anion drop generation rate is not too high, i.e., a rate that would flood the reactor tube or set up a competition for the cation, no heterogeneity results. To get longer reaction times one can slow down the cation flow, increase the number of loops, or both. When the anion drop generation rate is fixed, increasing the number of loops, as opposed to slowing the cation flow, results in less competition for the cation. There is a short residence time in the funnel before the anion drop is drawn into the stream and as long a s the reaction time is very much longer than the residence time, it will not contribute to heterogeneity.

Figure 3B:
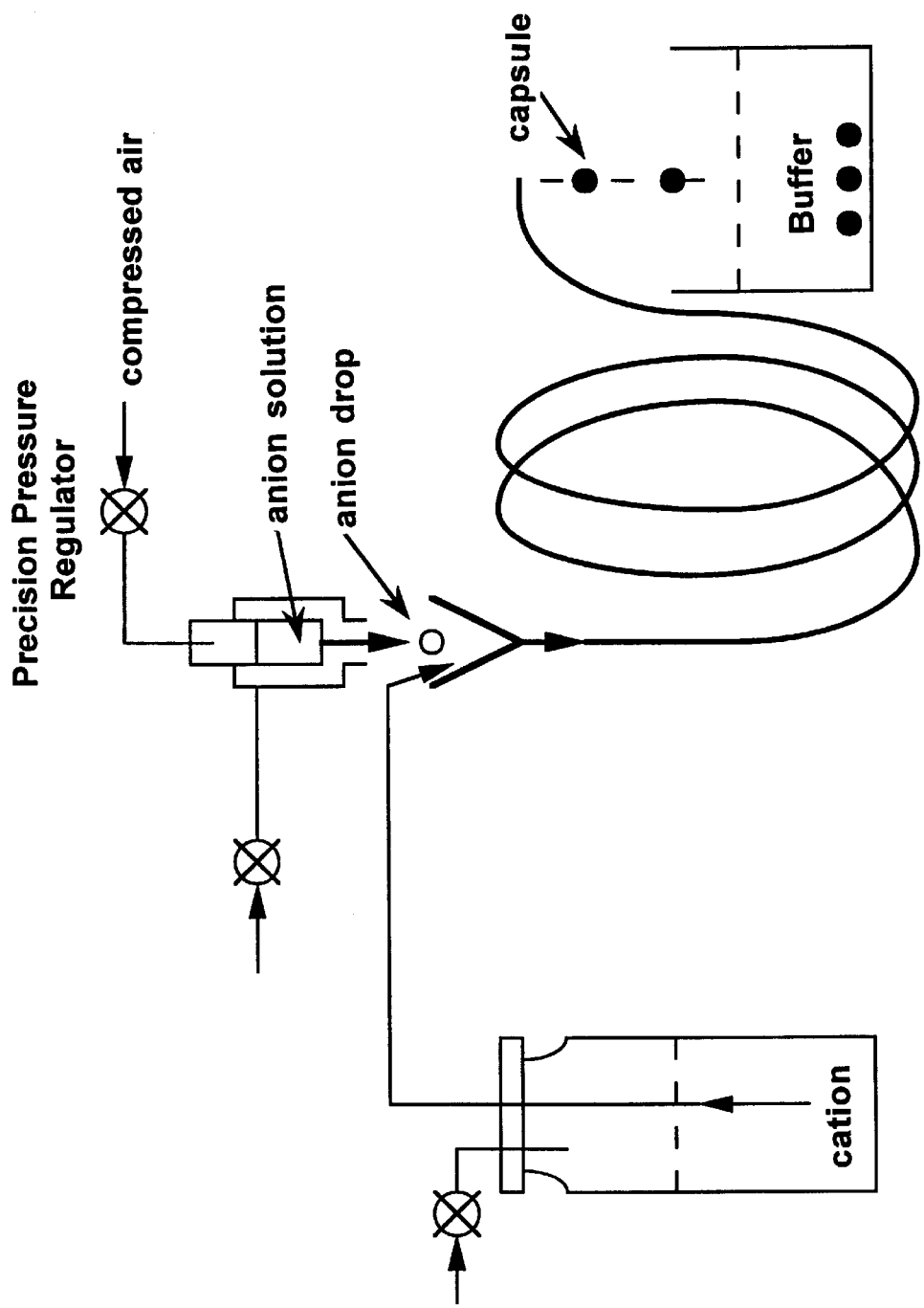

FIG. 3B is the schematic of the complete experimental layout, with a multi-loop reactor in operation. The extrusion of the anion and the delivery of the cation is accomplished by using compressed air, with precision pressure regulation. Additionally, the variations in flow rates during the course of an experiment run, resulting from hydrostatic pressure loss due to depletion of the liquid columns, are minimized (to less than 2%) by keeping the operating pressures high. A typical experiment has a pressure range of about 3–6 psi for anion and 5–10 psi for cation. In the case of the anion, the extrusion of the viscous liquid through a fine 22-gauge needle, serving as the nozzle, automatically requires a high operating pressure. In the case of the cation, the latter is accomplished b y using a long delivery line with a fine bore, or by throttling the normal delivery line.

Figure 10:
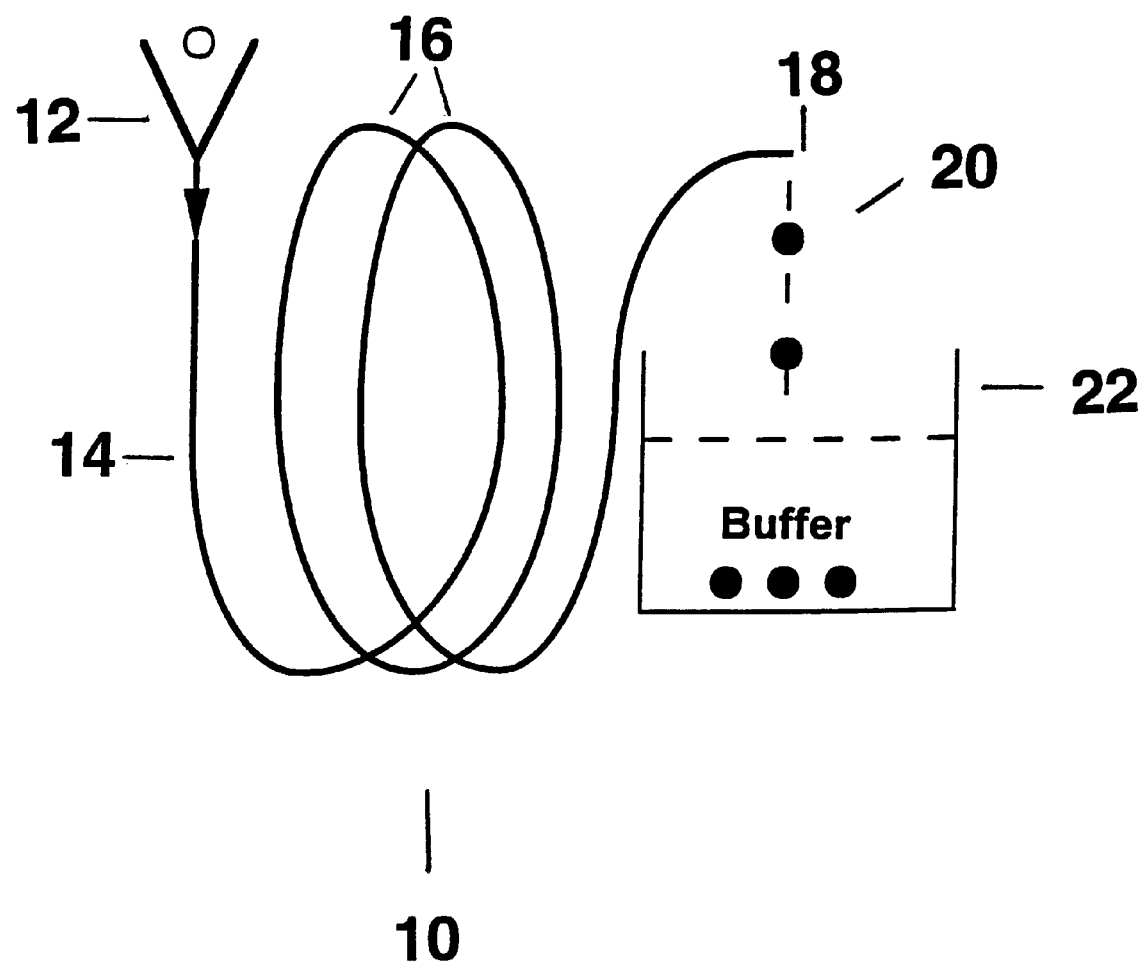
FIG. 10 shows a side view of one embodiment of the reactor of the present invention.

Referring to FIG. 10, a reactor constructed in accordance with an embodiment of the present invention is identified generally by the reference numeral 10. The particular reactor is shown with an entrance opening 12, in this case a funnel-shaped opening is shown. It is through the entrance opening 12 that drops of liquid to be encapsulated enter the stream in the reactor 10. The reactor 10 further includes a tube portion 14, which has two loops, indicated generally at 16, in this particular embodiment. A reactor constructed in accordance with the present invention m a y have numerous loops, depending on the reaction time desired for the capsule formation process.

The reactor 10 includes finally an exit opening 18 from which the formed capsules 20 are collected in some fashion; shown here is a beaker-type collector 22, containing an appropriate buffer. An alternative to a beaker-type collector is an additional tube with one or multiple loops, containing, e.g., a buffer or a leeching agent.

EXAMPLE 2

Capsule sedimentation: Comparison between a straight tube and a looped reactor

It is important to understand how the looped reactor keeps the particles suspended in the flow, vis-a-vis gravitational sedimentation. If the reactor loops were stretched out horizontally into a straight long tube, and the same volume fluxes could b e somehow sustained, other considerations arise. First, the looped reactor provides the economy of space—an equivalent straight tube would be very long and it would be difficult to follow the trajectories of the capsules. Second, precise pumping of the cation is required to sustain a desired volume flux in a straight tube. In other words, the self-adjusting feature of the looped reactor is an enormous advantage. Moreover, even if the straight tube were bent at the entrance and exit so as to encompass the self-adjusting feature, the two reactors still would not be the same.

It is not possible to manipulate the anion and cation such that the densities of the anion drops and of the forming capsules are so well matched with the cation liquid that sedimentation can b e prevented. Through a judicious choice of the operating parameters, however, sedimentation is overcome easily in the loop reactor but not in the straight tube design. First, the operating volume flux in a straight tube has to be about an order or more higher than that in a equivalent looped-reactor to keep the capsules afloat. This means that the rate of usage of cation is prohibitively high. Even so, all capsules can never be kept afloat for the entire process in the straight tube design. Some capsules will sediment and re-loft. This sedimenting/re-lofting process results in a significant loss of time and precise control of reaction time is lost. Sedimenting of the capsules during processing is the result of many factors, such as the flow field in the tube, the size of the capsules, the radial position of the capsules in the tube, and of course, the density of the capsules.

Figure 4A:
FIGS. 4a and b show the comparison of trajectories of a capsule in a straight tube (a) and in a reactor loop, with the same inner bore (b).
Figure 4B:
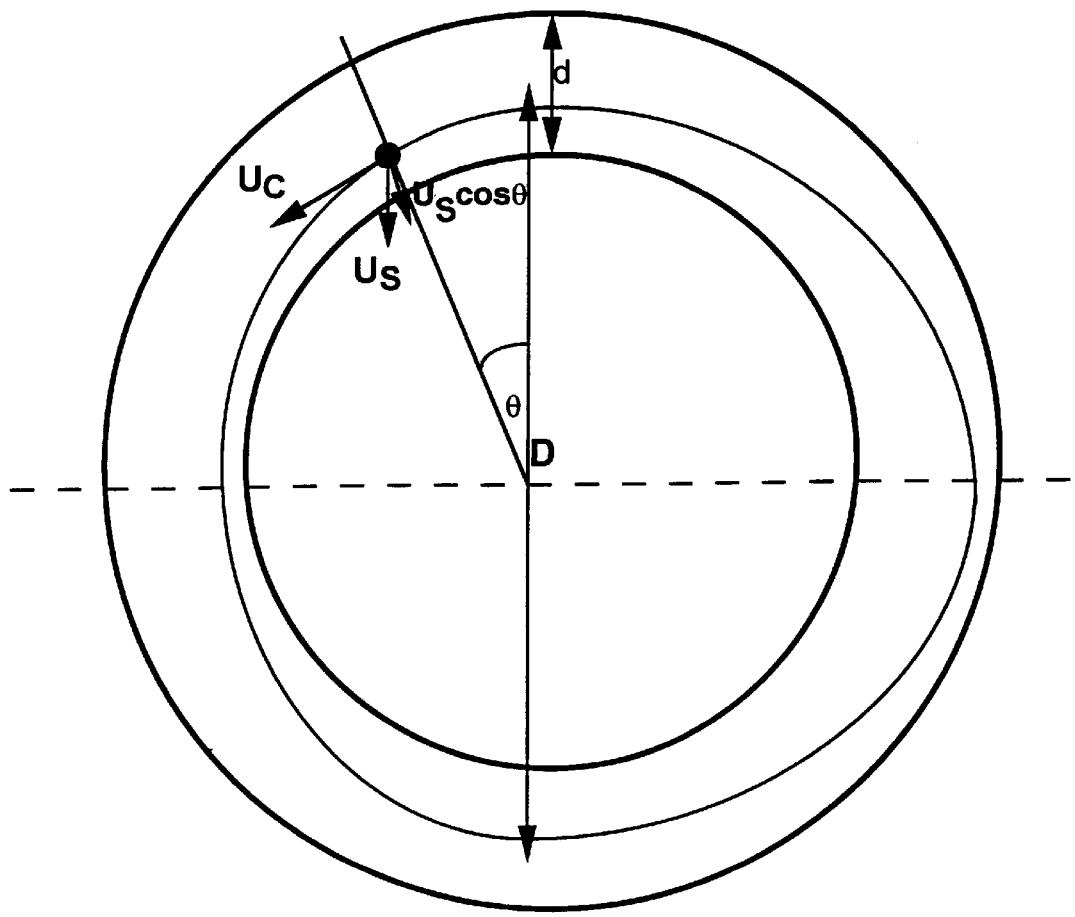
Figure 5A:
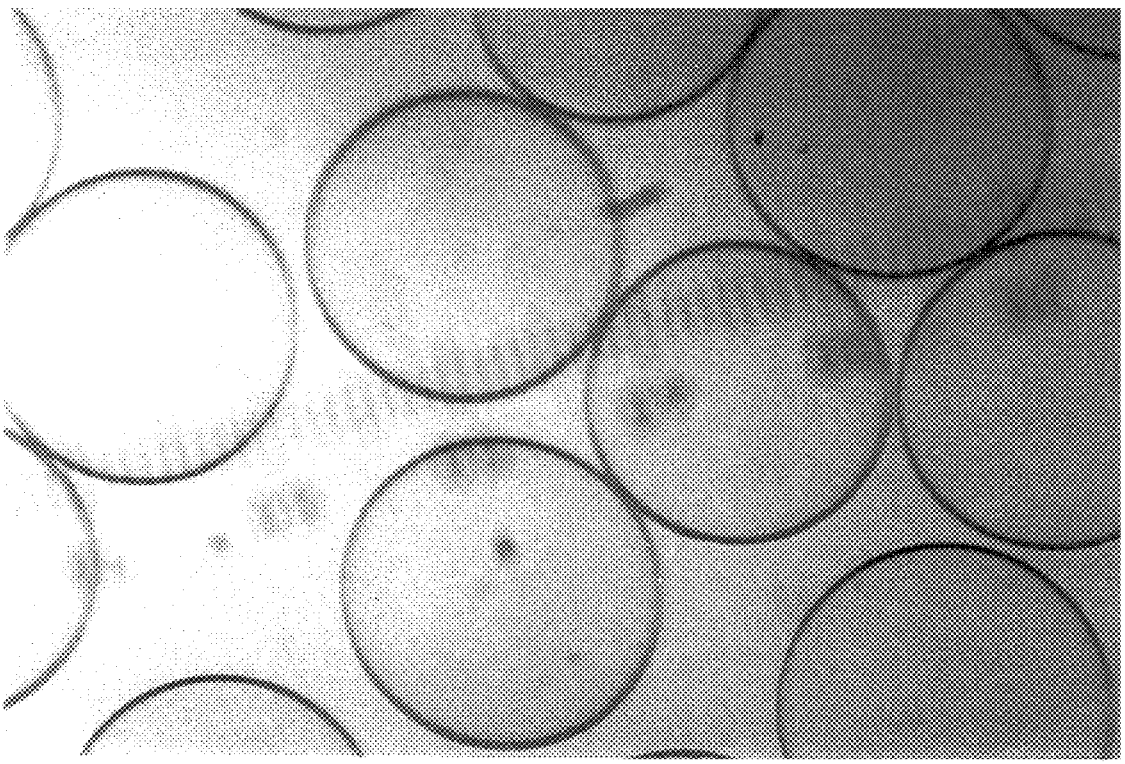
FIGS. 5a–d show the homogenous capsules produced in a capsule reactor for different reaction times: (a) 5 seconds, (b) 15 seconds, (c) 30 seconds, (d) 60 seconds
Figure 5B:
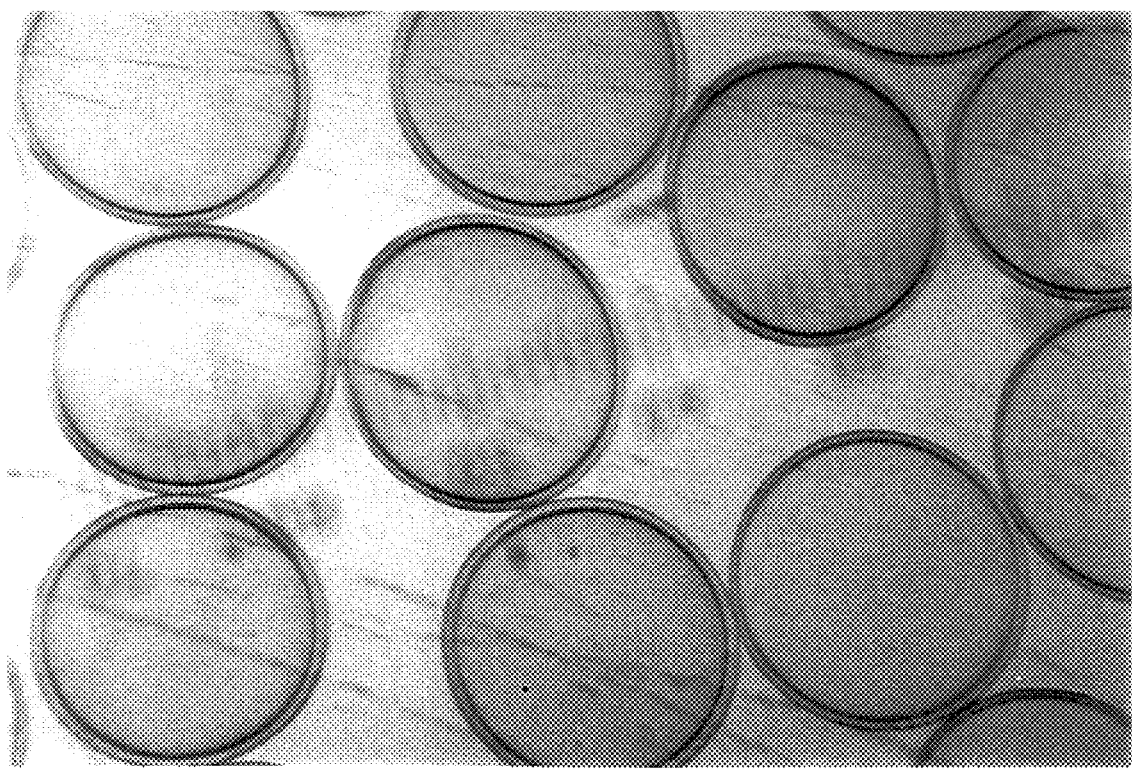
Figure 5C:
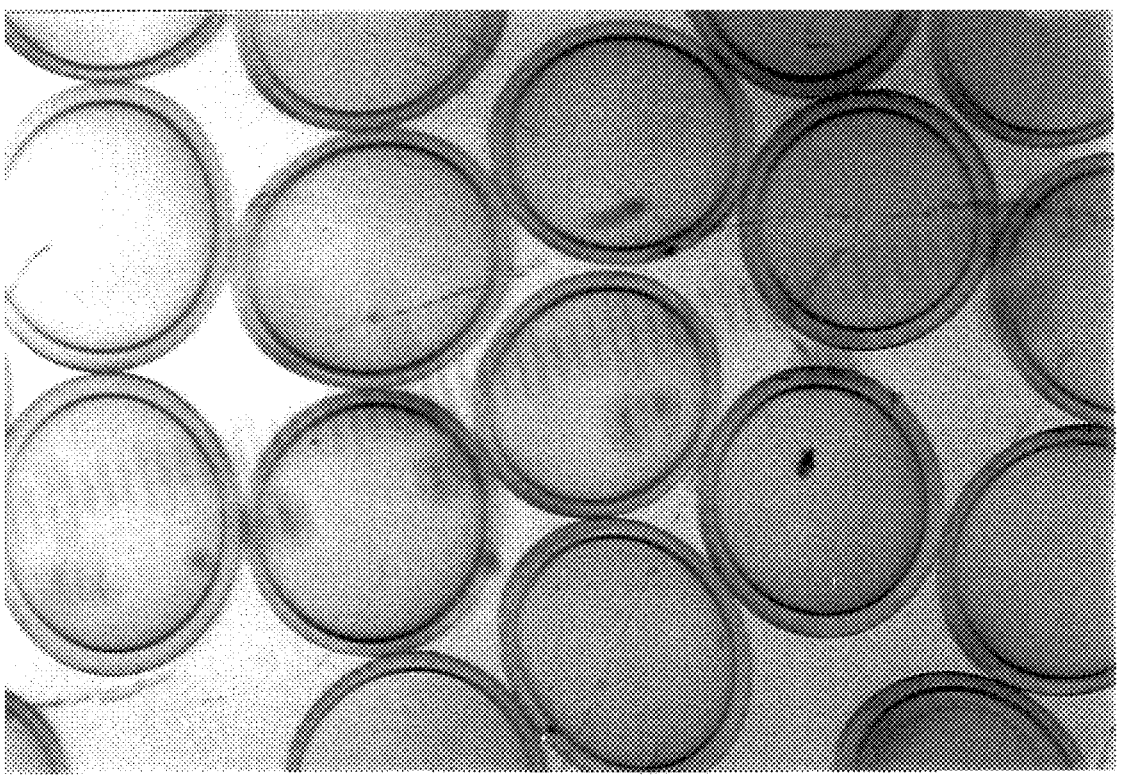
Figure 5D:
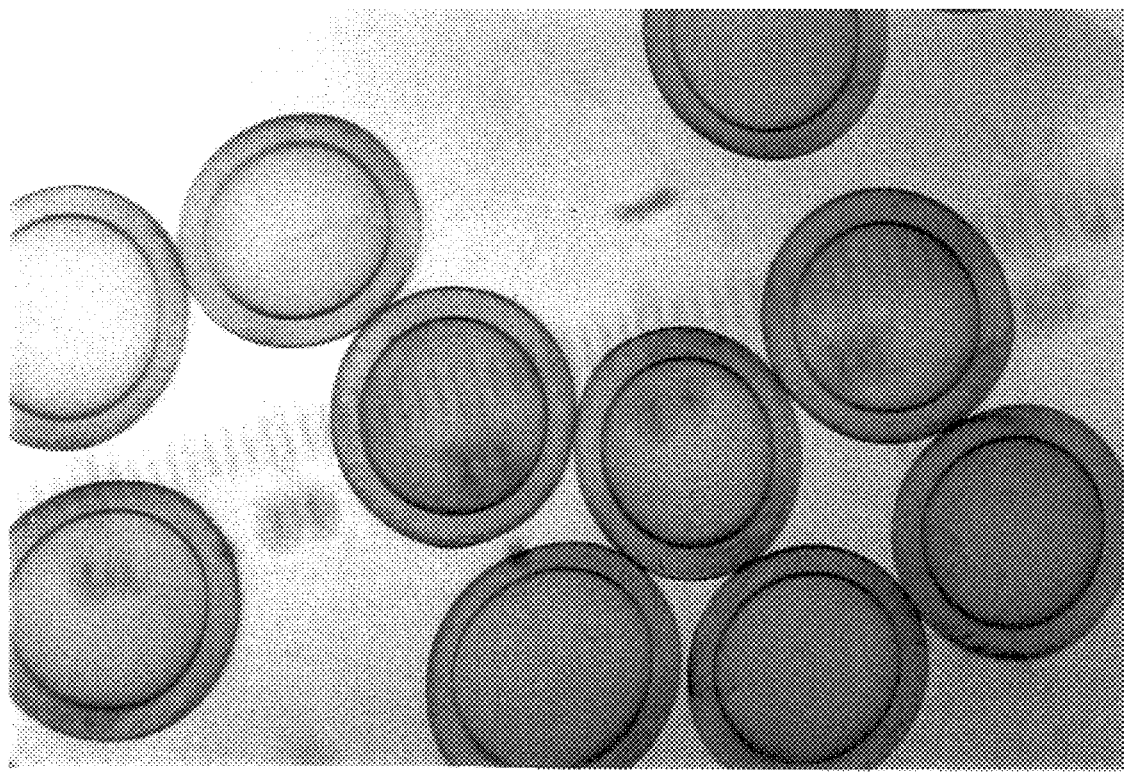

The key to precise wall thickness development is to ensure that each capsule "sees" the reaction for the same amount of time. This can be ensured in the loop reactor as the capsules are not prone to sedimentation. In the loop, the capsules "see" only a fractional gravity force in light of their trajectory (note: there is no noticeable role for centrifugal forces in the context of the operating volume fluxes and reactor loop dimensions for the centrifugal forces are about three orders of magnitude less than the force of gravity). FIG. 4A depicts a straight tube of inner diameter d, into which anion droplets are introduced, and the cation is pumped at a rate Q. FIG. 4B depicts a reactor loop, with the same tube inner diameter d.

To examine the trajectories of particles on the centerline, it can be assumed that the capsule is heavier than the reacting liquid (cation). In examining the straight tube reactor, the capsule at the centerline sediments on the bottom wall, if it travels downward a distance of d/2. The sedimenting time is approximately $d/(2 U_S)$; where $U_S$ is the sedimentation velocity. $U_S$ can be estimated using standard drag iterations (1).

Thus, $U_S \sim [4/3 \Delta\rho/\rho g d_p C_D]^{1/2}$ (Equation 1);

where $C_D$ is the drag coefficient:

$C_D \sim 24/Re(1+0.15Re^{0.687})$ for $1 < Re < 1000$ (Equation 2);

and where Re: Reynolds number ($d_p U_S$)/ν; ν is the kinematic viscosity of the cation liquid, $d_p$ is the capsule diameter, $\Delta\rho/\rho$ is the ratio of the density difference between the capsule ($\rho'$) and the cation ($\rho$) to the density of the cation.

The capsule convecting in the loop does not "see" the bottom of the tube, as the bottom is being continuously re-defined. Thus, the capsule is convected away from the bottom before sedimentation can occur. This property is a first consideration in establishing the critical volume flux criteria in a loop.

In the looped reactor (FIG. 4B), the tendency of gravity acting on the density difference $\Delta\rho$ between the capsule and the cation ($\Delta\rho=\rho'-\rho$) is to sediment the particle radially. The tendency of the convective flow is to convect the capsule in the loop, and presumably avoid sedimentation. Suppose the average convective velocity in the loop were $U_C$ (=Q/($\pi d^2$/4); Q: volume flux), then the criteria for keeping the capsule afloat are as follows:

First, the convective velocity must be greater than the sedimentation velocity, ie $U_C > U_S$; when $U_C = U_S$, the capsule is lofted from the wall at a point $\theta = -\pi/2$, where the component of gravity normal to the wall vanishes (FIG. 4B). Presumably a correlation of the form $U_C = M U_S$, where M>>1 being the experimentally determined constant, ensures that the capsule is kept lofted all through its path in the loop. However, a correlation of this type is specific to a particular reactor, and does not reflect explicitly the geometry of the loop (loop radius and tube inner diameter).

Second, the radial component of the sedimentation velocity $U_S \cos\theta$ (FIG. 4B), which is responsible for the capsule sedimenting on the wall, must result in a radial traverse of less than the tube inner diameter during the capsule transit through half a loop:

$$\frac{U_s}{U_c} < \frac{d}{D} \rightarrow U_c > U_s \frac{D}{d}$$ (Equation 3)

The criterion that $U_C > U_S D/d$ ensures that the capsule depicted in FIG. 4B will not collide against the wall during its transit through the loop. In a simple way, it links up the loop diameter (D) and the bore diameter (d), the two important design parameters in the reactor. The above calculations assume that the flow is uniform across the cross section of the tube, and does not take into account the nature of the fluid velocity profile in the tube and its role in keeping the particle afloat. Also, the relative size of the capsule in comparison with the bore size is not taken into account. Further, if the capsule starting point were radially different from the one considered, then it is bound to collide against the wall. If the capsule collides against the wall, the collision should not affect the performance of the reactor as long as the collision results in a rebound and not in capsule rolling on the wall leading to stall. A stall leads to failure of the process. While a criterion based on collision on a curved reactor surface, taking into account the fluid velocity profile and the capsule size, would be a more powerful one, a correlation of the form $U_C > K U_S D/d$ is expected, where the constant K can be determined from experiments as seen in Example 7; presumably K<1. In this way, sedimentation is avoided in the looped reactor, but isn't in the straight tube reactor.

EXAMPLE 3

Reactor Performance

The anion-cation system selected for demonstrating the performance of the reactor is the five-component CS/SA—PMCG/CaCl$_2$/NaCl system[2], with the following concentrations: anion: 0.6 g sodium alginate (SA) and 0.6 g cellulose sulfate (CS) in 98.8 g of phosphate buffered saline (PBS), cation: 1.8 g PMCG (poly methylene-co-guanidine), 1.0 g calcium chloride, and 0.9 g sodium chloride in 96.3 g of water (in general, for a chosen anion concentration, the relative concentrations of the cation components can be varied to get optimal capsule quality and performance).

Figure 6:
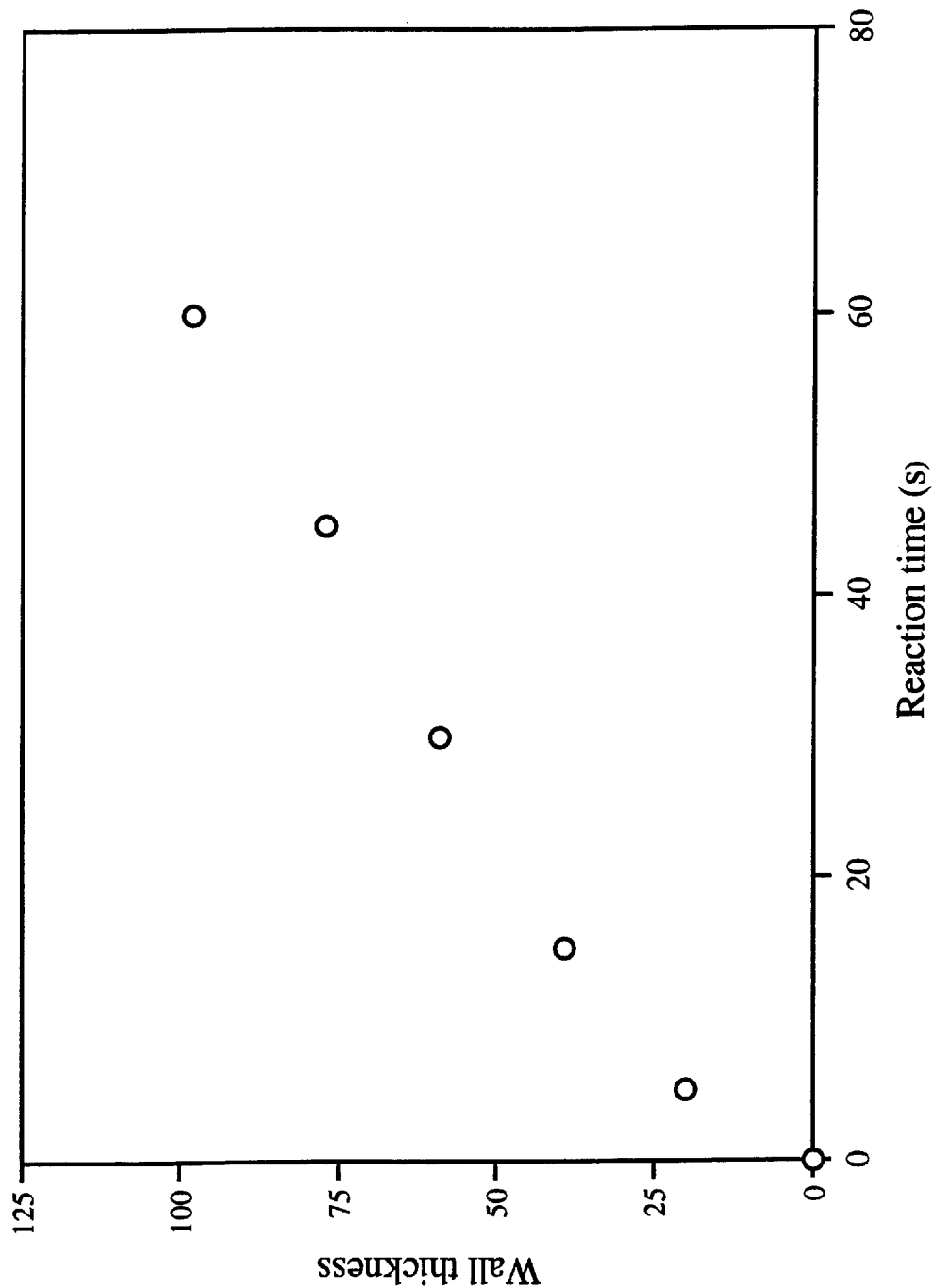
FIG. 6 shows the variation of capsule wall thickness with reaction time, for capsules of FIG. 5. Wall thicknesses are expressed in micrometers.

FIGS. 5A–D show the uniform capsules generated through the reactor of the present invention. Reactors with differing numbers of loops were used to get the different reaction times for making the capsules pictured. These capsules have been post-processed following reactor processing by quenching in buffer, and leeching in sodium citrate to make the capsule walls visible. Post-processing, depending on the initial wall thickness of the capsule causes swelling of the capsule to various sizes. This is true despite the fact that the initial starting size of the anion drops was the same. FIG. 6 shows the measured variation in wall thickness of the post-processed capsules, consequent to different reaction times. This wall thickness data is from intact, not sectioned, capsules, and has not been optically corrected.

EXAMPLE 4

Performance of a typical reactor

Figure 7:
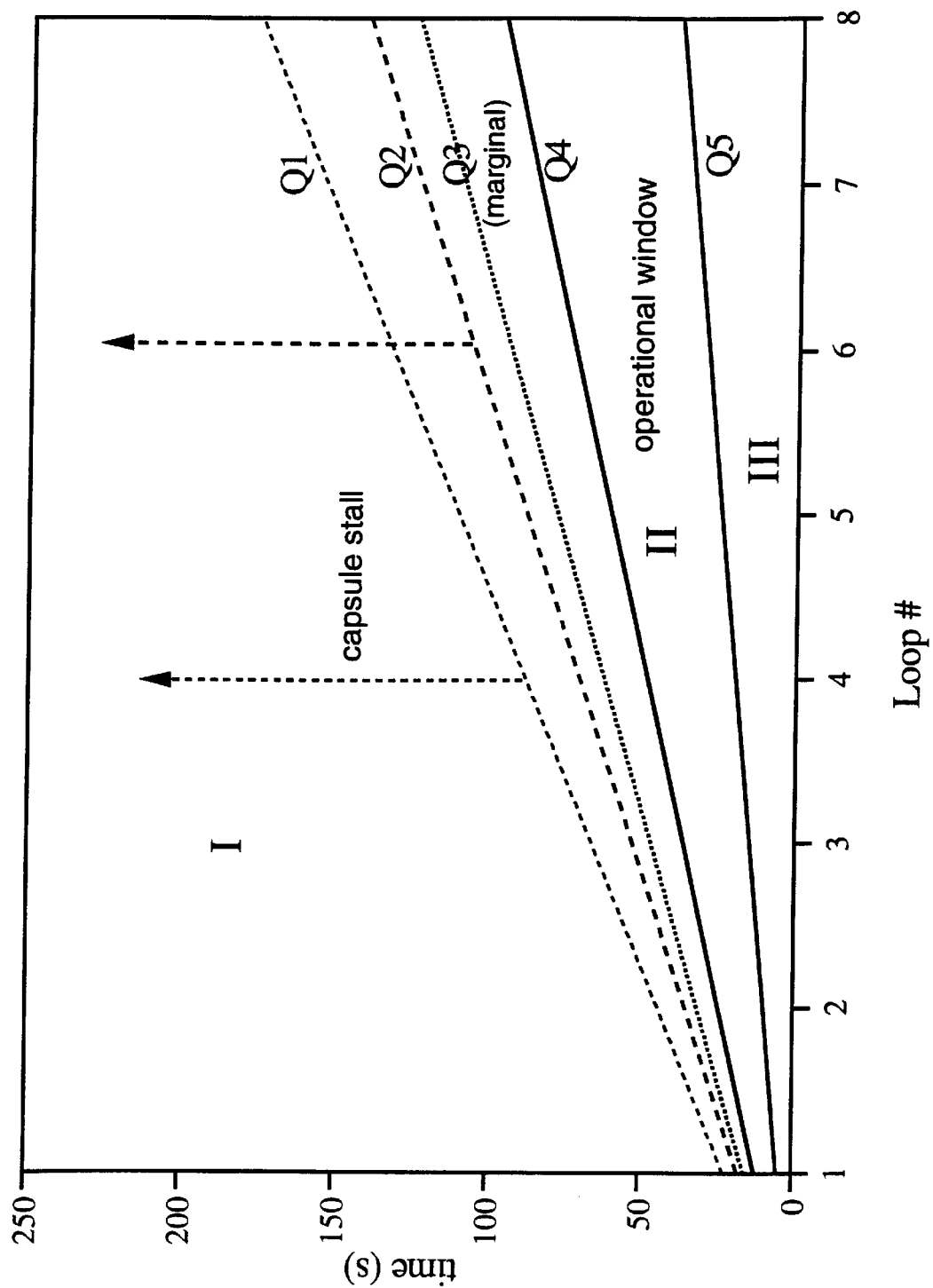
FIG. 7 shows the system performance chart for a typical eight loop reactor.

The performance of a typical reactor with eight loops of 11.2 cm loop diameter and 6 mm tube inner diameter is shown in FIG. 7. Along the way, many of the reactor operating principles, and limitations, are highlighted. A typical operating reaction time is 60 seconds. The equivalent cation volume flux is about 80 cc/min (for a reaction time of 80 seconds, the volume flux would be 60 cc/min.). The anion drops, about 0.9 mm in size, are generated at about 1000/minute, using a drop generator. FIG. 7 presents the observations of the capsule trajectories for different cation volume fluxes.

Figure 8:
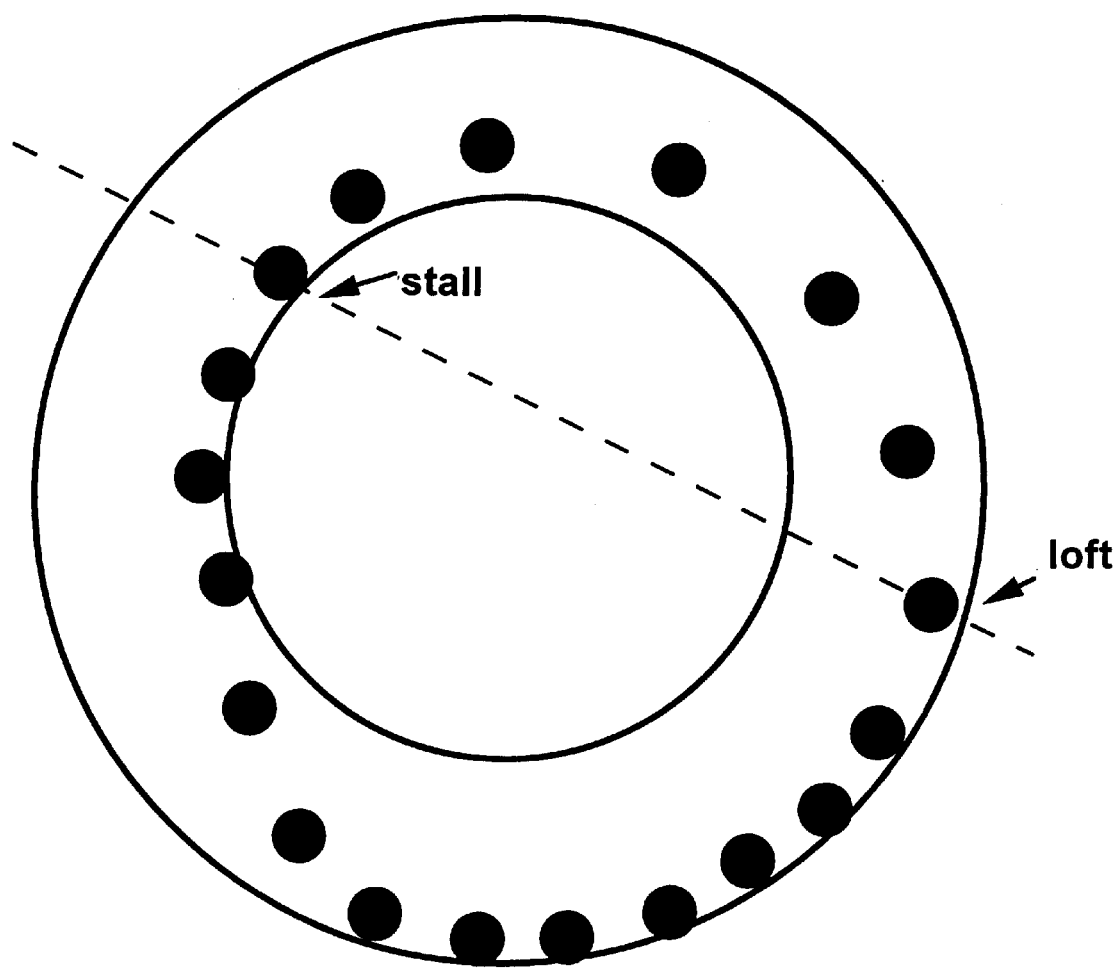
FIG. 8 shows the typical trajectory of a stalled capsule in the reactor loop.

If the cation flux were 26.5 cc/min (Q1), then capsules start stalling from the fourth loop onwards. Stalling is manifested by the lack of fluid drag on the capsules so that the capsules start accumulating and slowly rolling on the walls of the reactor. The experiment is lost at this stage, as there is no longer any control over reaction time. Capsules can be seen overtaking each other in the main body of the flow only to stall elsewhere. FIG. 8 schematically shows the trajectory of a single stalled capsule, at the early stages of the stall. More than half of its trajectory is spent on the walls, slowly spinning. The figure also approximately depicts the capsule speed in different parts of the loop.

If the cation flux were higher, say about 33 cc/min (Q2), then stall would occur after the sixth loop onwards. At 37 cc/min (Q3), the cation flux would be marginal—that is, the volume flux of the cation is barely sufficient for the capsules to make it through the reactor, without stalling. Thus, the first recommended flux has to be higher than Q3, e.g., 48 cc/min (Q4), and the reactor can be used as a linear time-reaction device for fluxes greater than this. Of course, reactors with fewer loops will have more relaxed restrictions on the volume flux.

The upper bound of the volume flux (Q5), is one of reactor design and anion droplet collection. As the volume flux increases, the hydrostatic head ($\eta$) increases. Clearly a limit is desired by design; however, there is also a limit to anion drop collection because the entry of the cation into the funnel results in some flow re-circulation. Depending on $\eta$, and the density mismatch between the anion drops and the cation, the drops reside in the funnel section for varying times. It is advisable to have a short column in the funnel; even if the cation flux has to be high, a short column in the funnel can still be maintained by lowering the height of the exit. Additionally, the upper bound of the volume flux (Q5) may also be dictated in a continuous production run, by the cation consumption pattern.

EXAMPLE 5

Hydrostatic head and flow Reynolds number

At a flux of 80 cc/min through a 6 mm bore, the average flow velocity ($U_C$) is 4.7 cm/sec, and the flow Reynolds number (Re=$U_C d/v$) is about 280. This is clearly laminar flow in the pipe—in fact, the flow is laminar for all the suggested cation flow rates. The entry condition for the flow to be a fully-developed laminar flow (Hagen-Poiseuille flow) is L>>Lo, where Lo is the entrance length. The accepted correlation for Lo is Lo/d~0.06 Re (3). In the present context, L/d is ~470, and Lo/d is ~17. That is, since the tube is extremely long compared with the entrance length, the entrance effects can be neglected, and one can proceed with the simple analyses for Hagen-Poiseuille flow. This principle applies to reactors with as few as two loops.

In Hagen-Poiseuille flow, the pressure drop $\Delta P$ for fully developed laminar flow of flux Q (cc/sec.) through a pipe of length L and diameter d, is given by:

$$\Delta P = \frac{128 \, \rho v L Q}{\pi d^4} \quad \text{Equation 4}$$

In the present invention, the pressure drop manifests as a hydrostatic pressure head $\rho g \eta$. Therefore one can establish a relation for $\eta$ as: $\eta = 128 \, v L Q / \pi \, g d^4$. For the current typical eight loop reactor, $\eta$ would be given by 0.9 Q. At 80 cc/min (1.33 cc/sec) the hydrostatic head is about 1.2 cm. and this was experimentally verified. Basically, from these equations one can gather that $\eta$ varies as the volume flux, and inversely as the fourth power of the tube bore. If the maximum tolerable head is 2 cm, then the flux cannot exceed 130 cc/min (Q5), in which case, the realizable reaction times for this eight loop reactor would be in the range 40–100 seconds, about three fold range, which is remarkable. Different reactors can be optimized, along similar principles.

EXAMPLE 6

Capsule Stall

A foremost fundamental question is why does a capsule stall in the reactor? If the capsule were in equilibrium with the flow to begin with, why does it end up on the wall? It cannot be due to the flow because it is steady, and, more importantly it is already fully developed with the boundary layers already merged. The answer lies in the capsule itself. The capsule density is continuously changing (increasing) as the membrane is forming, the larger the thickness, the higher the density of the capsule. This will be an issue regardless of what system is selected to run in the reactor.

Figure 9:
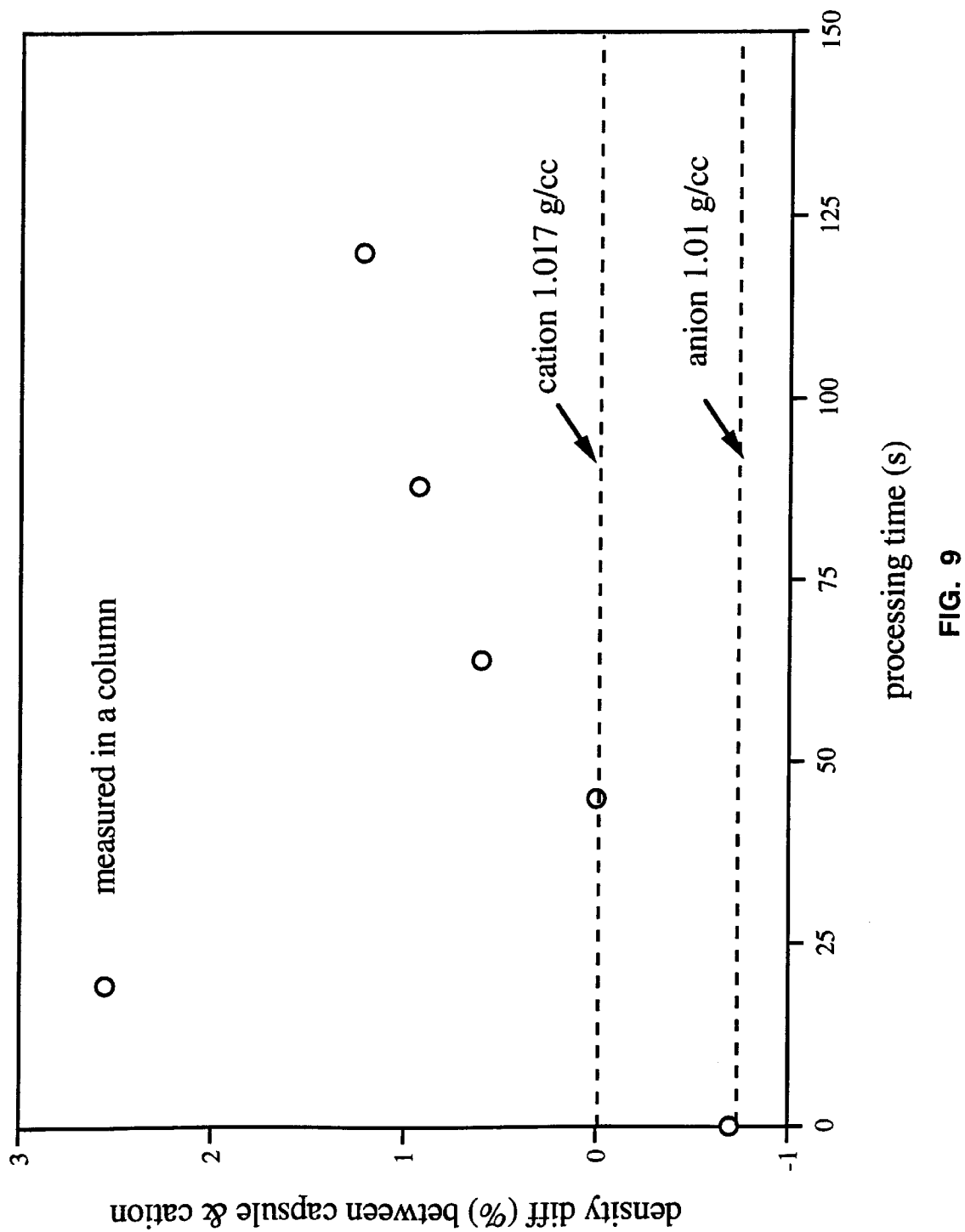
FIG. 9 shows the change in density of the capsule with reaction time (measurements in a vertical column of the cation).

In the CS/SA—PMCG/CaCl$_2$/NaCl system, the anion drops start about 0.7% lighter than the cation (FIG. 9), react, form membrane, start getting denser, match the density of the cation (FIG. 9) and then increase in density by a few percent, depending on the membrane thickness (the density of the capsule is greater by about 1.3% for a 120 second reaction time). So in essence, as the capsule is being convected by the flow field it runs foul, as its density increases (depending on reaction time). The flow simply cannot convect the capsule, and it stalls on the wall, inner or outer, depending on its position in the loop. As the flow rate is increased the capsule is re-suspended in the flow. The picture of capsule stall, at the early stages, is depicted in FIG. 8, where the trajectory of a stalled capsule is shown (this picture also applies to a snap-shot in time, showing the relative positions of stalling capsules). In the bottom half of the loop, the stalling capsules can be seen rolling on the outer bore wall, and in the upper half of the loop they can b e seen rolling on the inner bore wall. The re-lofting of the capsules, occurs at a point where the gravity vector is almost parallel to the wall. This picture depicts the early stages of stall; as the capsule stall proceeds, capsules pile up on one another, eventually choking the reactor.

In FIG. 7, if the cation flux were lower than Q1, e.g., 22 cc/min, then stall would occur in the first loop with capsules accumulating at the top of the loop and slowly rolling on the outer bore wall, since they are lighter than the cation. With the reaction proceeding, and capsule density increasing, the capsules would be resuspended in the flow. This stall is less dramatic and does not propagate, as does the one resulting when the capsule density is higher than density of the flow.

EXAMPLE 7

Comparison of experimental stall results with a model for capsule convection

The experimental observations on capsule stall were employed to establish the constant K for the simple model in Example 1, for a capsule avoiding sedimentation in the loop reactor. The recommended operating condition is $U_C$>K D/d $U_S$, $U_S$ is given by equation 1 in Example 2. When $U_C$=K D/d $U_S$, then critical reactor operation is expected, the capsules will stall, and the experimental observations on reactor stall, as noted in Example 4, can be used. The sedimentation velocity measurements, and, indirectly, the density of the capsules, were made by measuring the capsule velocities as they were reacting and sedimenting in a tall cation column. In this experiment, as the capsules are continuously reacting and getting denser, they never reach terminal velocities so the velocity measurements represent an instantaneous velocity at a given reaction time. However, at long reaction times (>80 seconds), the reaction rates are considerably slower and thus the velocity measurements reliably represent the average sedimentation velocities around those reaction times. Further, in the reactor of the present invention, the capsules are in constant state of agitation and presumably the capsule membranes form thicker making the capsules more dense than in the current tall column experiments. Nevertheless, the velocity measurements in the column provide a n upper bound on the value of K. However, if a similar measurement were made instead with reactor-processed then quenched capsules, using a column of water or PBS, the measured velocities would b e erroneous. This discrepancy is due to the osmotic interchange of the liquids occurring during quenching, or measuring, or both, which often results in capsule swelling. The net effect is an altered sedimentation velocity and density of the capsule. From the reactor performance data in Example 4:

a) For $U_C$ ~1.6 cm/sec (Q1), after a reaction time of 88 seconds, stall occurs from the fourth loop onwards. If one uses the measured sedimentation velocity of 0.3 cm/s around a reaction time of 90 seconds, then K is estimated to be about 0.29.

b) For $U_C$ ~2.25 cm/sec and the resulting reaction time of 125 seconds, stall is barely avoided through the eight loops of the reactor, with the cation flux being marginal. The measured sedimentation velocity at around 120 seconds, is about 0.4 cm/s. Using this value, one can estimate K to be about 0.3.

The recommended operating K is say at least about 30% higher than the critical K, thus about 0.4. This is a rule of thumb for experimental operation. If K is kept higher, then it is probable that there will be fewer capsule collisions on the reactor wall. The collisions by themselves appear to be of the grazing type, aided by the curved trajectory in the looped reactor. Following collision, if there is no rebound then the capsule starts rolling on the outer wall, leading to a stall.

The fact that the experimentally-determined constant K is much less than 1, implies that the model may not capture all the facets of capsule motion. In particular, the model does not take into consideration the role of the shear flow field in keeping the capsule lofted, and the role of the capsule size in comparison to the diameter of the tube bore. A more accurate model of reactor performance can be had only through a rigorous theoretical framework dealing with capsule motion through a looped-reactor and its collisions on the curved wall, and establishing conditions for grazing collisions and lofting.

If the reactor operating conditions and the wall thickness requirements optimally were chosen such that the variability in capsule density is −2% to +2% under all operating conditions, then good capsules can be generated. The entry level issues of varying residence times can be minimized by matching the densities of the anion and cation, minimizing the tendency of the drops to remain in the funnel longer, by getting drawn into the re-circulating flow. Preferably, the anion should be slightly denser than the cation. In either case the penalty paid is an earlier potential stall in the reactor. However, as seen herein, stall can be avoided by increasing the cation volume flux.

EXAMPLE 8

Capsule Processing

Capsules were made in the reactor of the present invention. A multi-loop chamber reactor was filled with cation solution. The cation solution bath was fed by a cation stream which continuously replenished the solution and carried away the anion drops being introduced into the chamber. SA/CS droplets, with pancreatic islet cells enclosed, entered the $PMCG/CaCl_2/NaCl$ stream at an oblique angle, so as to minimize the islet decentering and drop deformation problem associated with impact. The droplets were then carried into the multi-loop reactor by the polycation stream. The reactor allowed for adjustment of reaction time and, due to the loop construction, gravitational effects were negated. These features facilitated tight control of capsule sphericity, membrane thickness and uniformity. Using the reactor, capsules were produced with diameters from 0.5 mm to 3.0 mm and membrane thicknesses from 0.006 mm to 0.125 mm.

A novel chemical reactor has been designed and developed to generate uniform capsules. The operation highlights and parameters for use of this novel reactor are presented herein. The reactor helps to control precisely the reaction time between reacting anion drops and a cation stream, leading to uniform-sized capsules with walls of virtually identical thickness. In addition, the mild tumbling of the capsule during transit through the reactor, ensures that the capsule wall of each individual capsule is uniformly thick all around. In the reactor of the present invention, a very optimal usage of cation is effected. Additionally, the reactor can be tailored to meet any reaction time requirement. In a preferred embodiment, conditions should be selected such that the density fluctuation of the capsule throughout its entire journey through the reactor is less than 2%.

The following references were cited herein:
1. Wallis, G. B., *One-Dimensional Two-Phase Flow*, McGraw-Hill Inc., 1969.
2. T. G. Wang, et al., 'A new generation capsule and encapsulation system for immunoisolation of pancreatic islets', in press: *Nature: Biotechnology* (1977).
3. White, F. M., *Fluid Mechanics,* McGraw-Hill Inc., 1986.

Any patents or publications mentioned in this specification are indicative of the levels of those skilled in the art to which the invention pertains. These patents and publications are herein incorporated by reference to the same extent as if each individual publication was specifically and individually indicated to b e incorporated by reference.

One skilled in the art will appreciate readily that the present invention is well adapted to carry out the objects and obtain the ends and advantages mentioned, as well as those inherent herein. The present examples along with the methods and procedures described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A reactor for continuously making uniform capsules from two fast reacting charged, polymeric liquids, comprising:

(i) a means for providing a quiescent, steady, and continuous stream of a first reacting liquid through a reactor tube;

(ii). a means for delivering a steady stream of uniformly-sized drops of a second reacting liquid into said continuous stream of a first reacting liquid into an entrance opening of said reactor tube;

(iii). said reactor tube, having at least one loop and at least two openings wherein one of said openings is at a first end of said tube and is said entrance opening, and wherein one of said openings is at a second end of said tube and is an exit opening, and wherein said exit opening is at a height substantially equal to said entrance opening; and, (iv). a collector with buffer liquid at said exit opening, for quenching the reaction.

2. The reactor of claim 1, wherein said entrance opening has a funnel shape.

3. The reactor of claim 1, wherein said exit opening is connected to a second tube portion, wherein said second tube portion has at least three openings and at least one loop, a first opening for collection of said capsules, a second opening for introducing buffer into said second tube portion so as to create a buffer stream, and a third opening for collecting said capsules treated in said buffer stream in said second tube portion.

4. The reactor of claim 1, further including means for providing a pressure in said reactor of about 2 psi to 10 psi.

* * * * *